United States Patent [19]
Palmer, III et al.

[11] Patent Number: 4,785,481
[45] Date of Patent: Nov. 22, 1988

[54] EYE PROTECTION DEVICE

[76] Inventors: Francis R. Palmer, III; Robyn-Faehnrich Palmer, both of 3901 Los Feliz Blvd., #101, Los Angeles, Calif. 90027

[21] Appl. No.: 80,910

[22] Filed: Aug. 3, 1987

[51] Int. Cl.⁴ .......................................... A61F 09/02
[52] U.S. Cl. ................................... 2/436; 2/13; 2/428; 2/429; 2/437; 2/448; 2/449; 2/450
[58] Field of Search ............... 2/436, 437, 428, 429, 2/448, 449, 450, 13; 351/44, 111

[56] References Cited

U.S. PATENT DOCUMENTS

| | | | |
|---|---|---|---|
| 2,403,223 | 7/1946 | Kaesz | 2/13 |
| 2,877,463 | 3/1959 | Watkins | 2/437 |
| 3,011,170 | 12/1961 | Lutz | 2/13 |
| 3,141,172 | 7/1964 | Hirschmann | 2/436 |
| 3,395,406 | 8/1968 | Smith | 2/436 |
| 3,418,658 | 12/1968 | Danico | 2/436 |
| 3,436,761 | 4/1969 | Liautaud et al. | 2/13 |
| 4,027,342 | 6/1977 | Hirschmann, Jr. | 2/436 |
| 4,306,779 | 12/1981 | Rege | 2/448 X |
| 4,353,134 | 10/1982 | Macnabb | 2/428 |

Primary Examiner—Werner H. Schroeder
Assistant Examiner—Jeannette E. Chapman
Attorney, Agent, or Firm—John J. Posta, Jr.

[57] ABSTRACT

The device is in the form of a pair of specially designed glasses, goggles or an eye mask sealingly engaging the wearer's head. In each case, a frame includes a front support bearing one or more transparent, preferably prescription-ground lenses or eye shields, and a pair of side supports connected thereto. Components are connected to or built into the frame to allow free passage of air to the eyes while blocking contaminant-bearing liquids and solids. Thus, in one embodiment, eyeglasses are fitted with two sets of triangular preferably air permeable flexible sheets. One set of sheets depends from the side supports and is connected to the sides of the front support, with the other pair is connected to the side and front supports above the latter, being connected at its rear end to slides in the top of side support channels to permit easy folding of the glasses. In two other embodiments, goggles and eye masks bear air vents fitted with liquid and solid-blocking filters. Such filters may be replaced and may be sandwiched between screens within outer vented boxes.

10 Claims, 3 Drawing Sheets

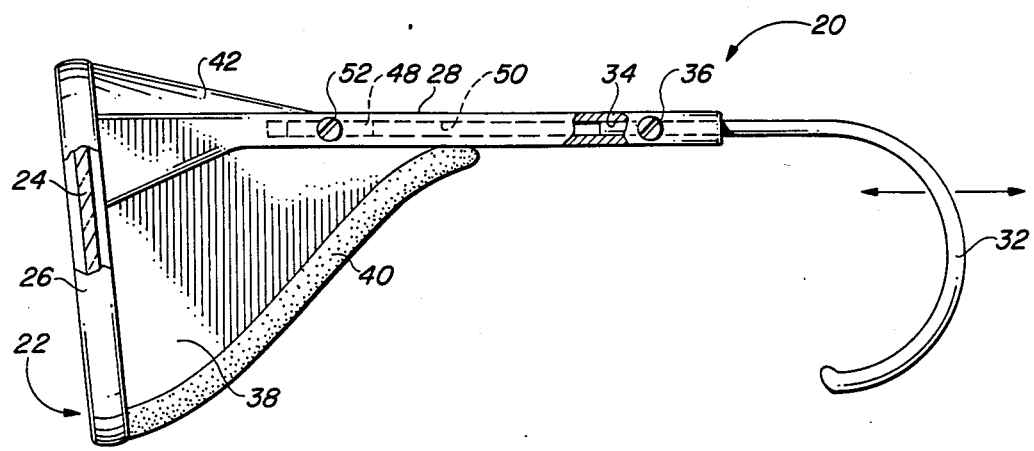
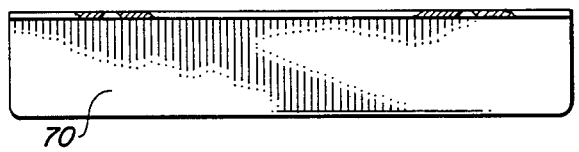
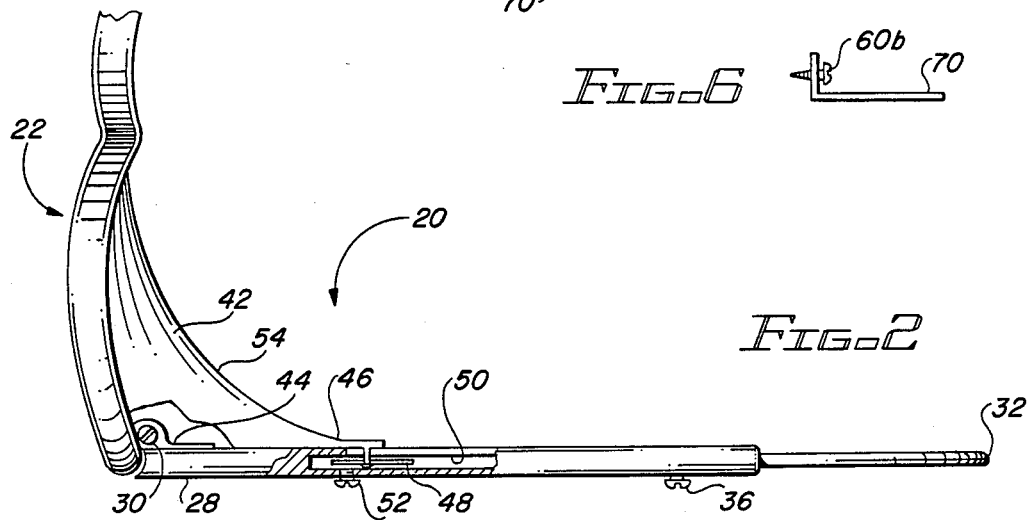
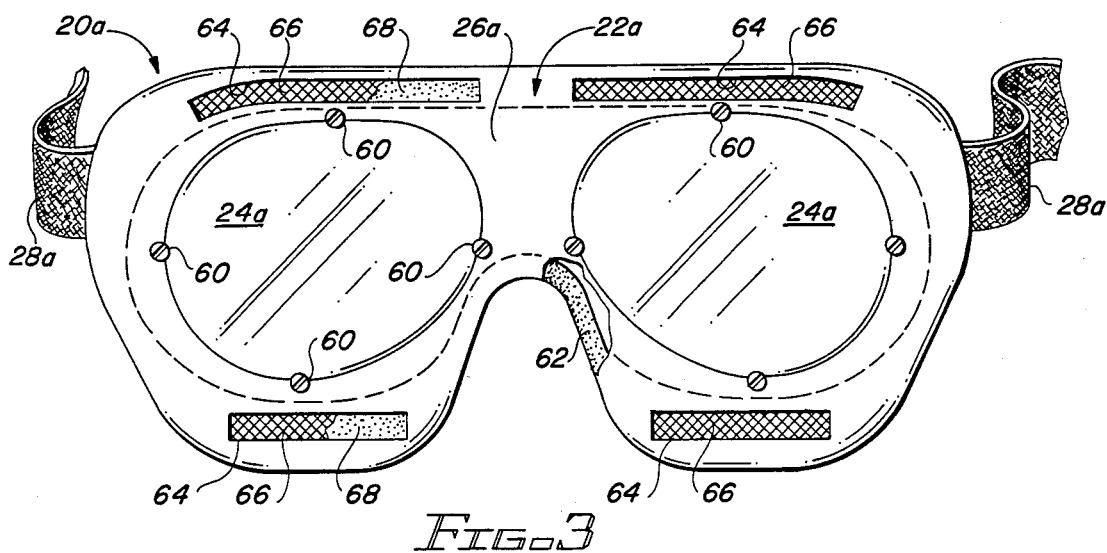

EYE PROTECTION DEVICE

BACKGROUND OF THE INVENTION

1. Field of the Invention

The present invention generally relates to eye protection devices and, more particularly, to an improved type of such devices permitting access of air to the eyes while blocking passage of liquid-and solid-bearing contaminants.

2. Prior Art

Conventional cloth masks and sometimes eyeglasses are routinely used by surgeons during operations, including those in which dangerous liquid-transmittable contagions, such as the AIDS virus, are present. In those instances, the surgeon is running a great risk of having AIDS-bearing liquid or solid and other contagious liquid or solid matter splash up into the surgeon's eye, allowing it to enter the surgeon's body and cause the disease. Sealing the surgeon's face behind an impermeable mask is not practical, because operations frequently take a long time and the mask will become too hot to comfortably wear and will fog over, obscuring the surgeon's view.

Accordingly, there is a need for an improved eye protective device usable by surgeons and other medical personnel in contact with patients having liquid and/or solid-transmittable contageous disease. Such device should protect the eyes, and yet be comfortable and prevent fogging and obscuring of the field of vision.

SUMMARY OF THE INVENTION

The improved eye protective device of the present invention satisfies all the foregoing needs. The device is substantially as set forth in the Abstract. Thus, it comprises specially designed eyeglasses, prescription goggles or an eye mask.

In each instance, the device includes a frame having a front support bearing one or more transparent preferably prescription ground lenses or an eye shield, and a pair of side supports connected thereto. The frame bears components which allow the free passage of air to the eyes while blocking contaminant-bearing liquids and solids.

In one embodiment, eye glasses are fitted with two sets of triangular preferably air-permeable, flexible sheets of plastic or the like. Both sets are connected to the front and side supports, one set depending below the side supports to provide side shielding and the other set extending from the front support corners rearwardly above and connected to the side supports to provide corner and above-the-eye shielding. The sets are preferably collapsable to allow the glasses to be folded.

In other embodiments, goggles and eye masks are sealed to the face around the head with relatively flexible frames and/or cushioning, but air access to the face is provided through air vents fitted with filters which block liquids and solids. Therefore, comfort and eye protection are afforded with all embodiments of the present invention, without fogging of eye glass and goggle lenses and eye mask shields.

Further features of the invention are set forth in the following detailed description and accompanying drawings.

DRAWINGS

FIG. 1 is a schematic side elevation, partly broken away, of a first preferred embodiment of the improved eye protection device of the present invention;

FIG. 2 is a schematic, fragmentary top plan view of the device of FIG. 1;

FIG. 3 is a schematic front elevation, partly broken away, of a second preferred embodiment of the improved device of the present invention;

FIG. 5 is a schematic top plan view of the plate of FIG. 4;

FIG. 6 is a schematic side elevation of the plate of FIG. 4;

DETAILED DESCRIPTION

FIGS. 1 and 2

Figure 4:
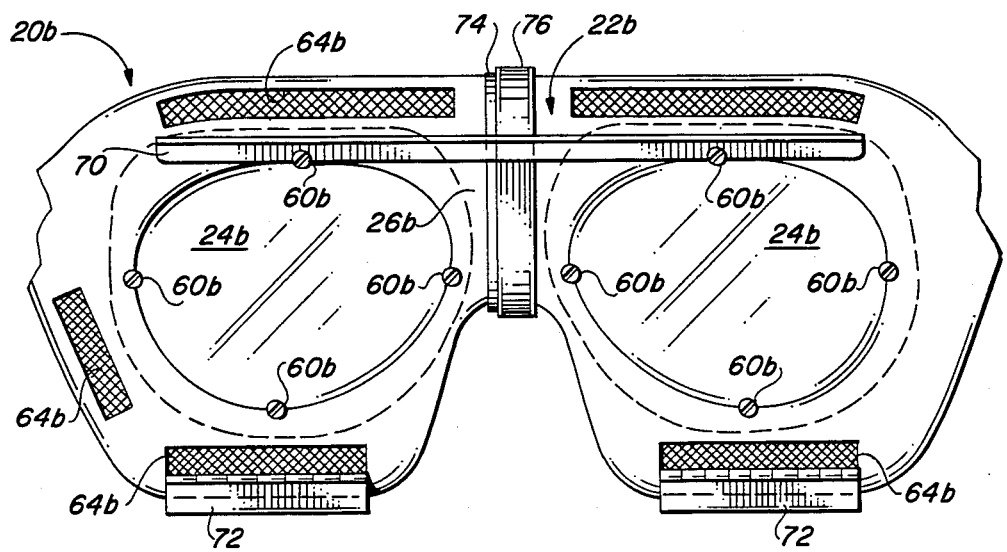
FIG. 4 is a schematic front elevation, partly broken away, of a third preferred embodiment of the improved device of the present invention, including a top air vent shield plate.

Now referring more particularly to FIGS. 1 and 2 of the accompanying drawings, a first preferred embodiment of the improved eye protection device of the invention is schematically depicted therein. Thus, device 20 is shown which comprises an eyeglass frame 22 bearing a pair of preferably prescription ground glass or plastic lenses 24 in the generally vertical front frame support portion 26 thereof.

The frame also includes a pair of side supports 28 connected by hinges 30 to the sides of front support 26 and extending rearwardly thereof to terminate in hook-shaped ear pieces 32 slideably received in channels 34 thereof and pinned at selected positions by adjustable side screws 36 bolts or the like to permit device 20 to be adjusted to the wearer's head for a close fit. Frame 22 can be made of metal, plastic, wood, ceramic or the like suitably padded or cushioned with elastomeric material for comfort and desired shielding.

Device 20 includes a generally triangular pair of side shields 38 which are connected to frame support 26 and to side supports 28 and depend from the latter as shown in FIG. 1, or they may be connected to side supports 28 and come to rest against frame support 26 when the side supports 28 are in the unfolded position. Shields 38 may have a cushioned rim 40 and may be fabricated of any suitable flexible resilient material which hugs the sides of the wearers face for protection against passage of liquid and solid, but which bends or folds to permit side supports 28 to be folded against front support 26 for storage of device 20. Preferably, the material of shields 38 is also air permeable while blocking liquids and solids, so as to be cool and comfortable to wear. Such material is preferably an air permeable sheet of plastic well known in the plastic art.

A second pair of similar protective, generally triangular, flexible shields 42, preferably air-permeable but capable of blocking liquids and solids, is connected to front support 26 above side supports 28 but extends rearwardly for attachment to the latter so as to cover the corners 44 of frame 22 and abut the side edges of the wearer's brow for sealing protection. The rear ends 46 of shields 42 are connected to slides 48 in channels 50 in the tops of side supports 28 and are releasably pinned in place by screws 52. Shields 42 slide and fold when side supports 28 are folded against front support 26. The exact curvature of the wearer's side brow is resiliently abutted by the curved edge 54 of shields 42 for the best possible protective fit. Liquids and solids cannot enter the wearer's eye from over the top of frame 22 due to shields 42.

Accordingly, device 20 is a pair of eyeglasses of an improved, non-fogging, fully protective type ideally suited for wear by a surgeon or the like while operating on contagious patients.

FIG. 3

A second preferred embodiment of the present device is schematically depicted in FIG. 3. Thus, device 20a is shown. Components similar to those of FIGS. 1 and 2 bear the same numerals, but are succeeded by the letter "a". Device 20a is similar to device 20, but is a pair of goggles bearing preferably prescription lenses 24a releasably secured by screws 60 to soft flexible resilient frame 22a, specifically front support 26a thereof, to which adjustable flexible side straps 28a are connected. A portion 62 of device 20a may be padded for a better fit and for improved comfort.

Frame 22a effectively prevents ingress of contaminant-bearing liquids and solids to the eyes of the wearer, while also containing a plurality of air vents 64 therethrough to assure that cooling air circulates behind lenses 24a so that the wearer is kept comfortable and lenses 24a don't fog. Air vents 64 bear screens 66 holding air permeable filters 68 in place in vents 64. Filters 68 prevent transmission of liquid and solids therethrough and may be, for example, air-permeable plastic such as may be used in shields 38 and 42, or multi-ply filter paper, cellulosic material, porous ceramic, fiberglass, or other known filter material. Device 20a has substantially the advantages of device 20.

FIGS. 4, 5 and 6

A third preferred embodiment of the improved device of the present invention is schematically depicted in FIG. 4. Thus, device 20b is shown. Components thereof similar to those of device 20 or 20a bear the same numerals, but are succeeded by the letter "b". Device 20b is substantially identical to device 20a, but differs as follows:

(a) side air vents 64b are added;
(b) top air vents 64b are further protected from flooding by liquid and solids during surgery by a detachable shield plate 70 which is L-shaped in side elevation (FIG. 6) and is releasably connected over lenses 24b by top screws 60b;
(c) bottom air vents 64b are provided with depending hinged lids 72 which can be set at rt. angles thereto to protect those vents 64b; and,
(d) front support 26b is provided with central telescoping parts 74 and 76 to adjust the lateral distance between lenses 24b for the best possible fit.

Device 20b has the other advantages of devices 20a and 20.

Figure 7:
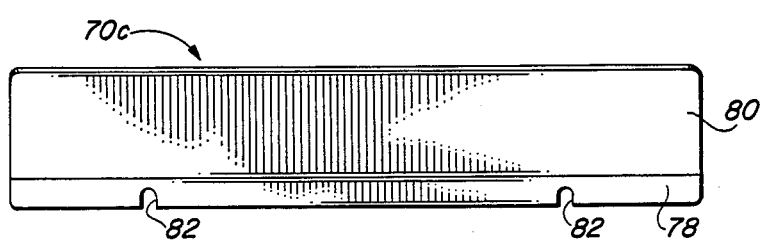
FIG. 7 is a schematic top plan view of a modified version of the plate of FIG. 4.
Figure 8:
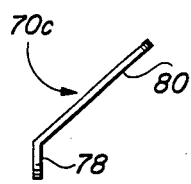
FIG. 8 is a schematic side elevation of the plate of FIG. 7.

FIGS. 7 and 8

A modified version of plate 70 is shown in FIGS. 7 and 8. Thus, plate 70c is shown comprising a vertical portion 78 and a portion 80 sloping upwardly therefrom at an abtuse angle. Portion 78 is provided with notches 82 through which screws 60b fit to connect plate 70c to device 20b in place of plate 70.

Figure 9:
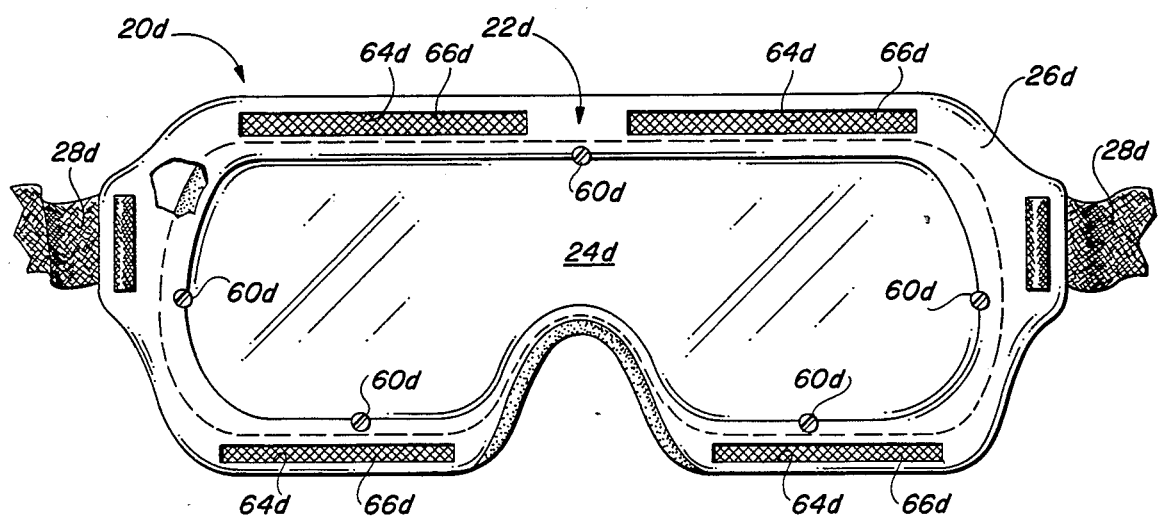
FIG. 9 is a schematic front elevation, partly broken away, of a fourth preferred embodiment of the improved device of the present invention.
Figure 10:
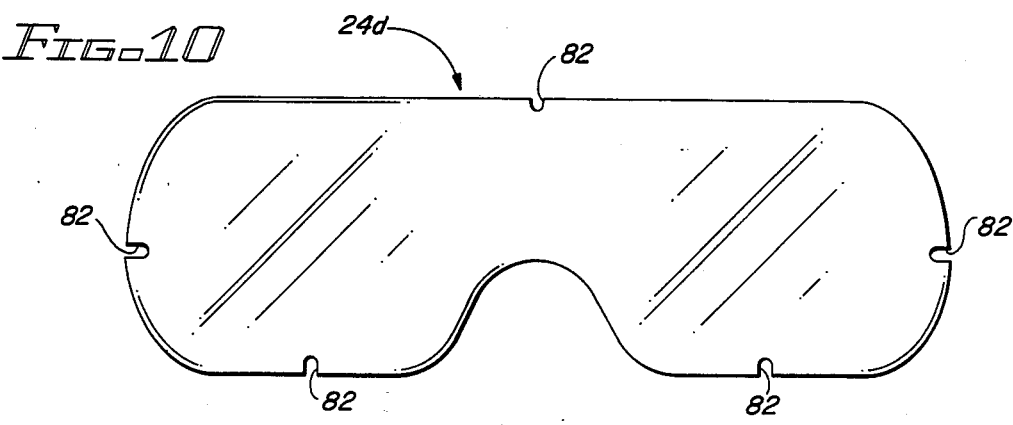
FIG. 10 is a schematic front elevation of the eye plate of the device of FIG. 9.
Figure 11:
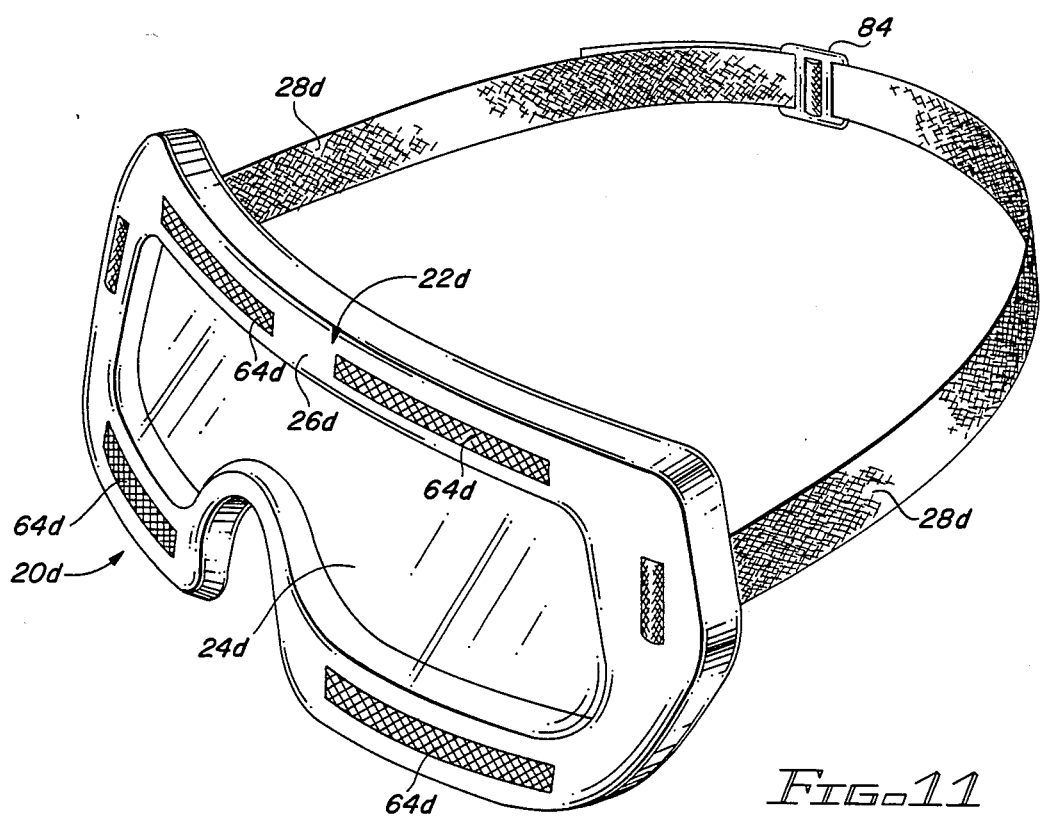
FIG. 11 is a schematic perspective view of the device of FIG. 9.

FIGS. 9, 10 and 11.

A fourth preferred embodiment of the improved device of the present invention is schematically depicted in FIGS. 9, 10 and 11. Thus, device 20d is shown. Components thereof similar to those of devices 20, 20a or 20b bear the same numerals, but are succeeded by the letter "d". Device 20d differs from device 20a only as follows:

(a) device 20d is an eye mask designed to be worn over the eyes directly or over glasses;
(b) a single lens plate or transparent shield 24d spans the width of frame 22d, which is relatively inflexible but internally padded, and is connected thereto by screws 60d passing through notches 82 in plate 24d.

As with device 20a, flexible straps 28d are connected to each other, as by buckle 84 (FIG. 11) and to front support 26d, which bears air vents 64d with screens 66d and filters 68d.

Figure 12:
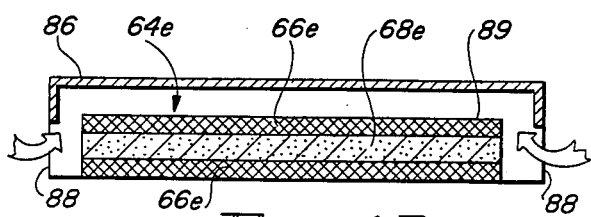
FIG. 12 is a schematic longitudinal cross section of an air vent and filter array usable in the device of FIG. 9.
Figure 13:
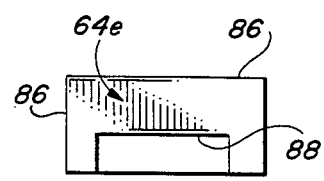
FIG. 13 is a schematic side elevation of the array of FIG. 12.
Figure 14:
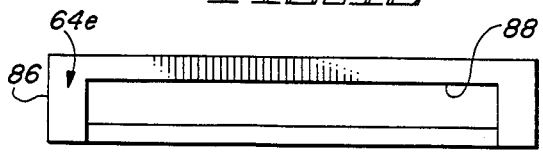
FIG. 14 is a schematic front elevation of the array of FIG. 12.

FIGS. 12, 13 and 14

Now referring to FIGS. 12, 13 and 14, an improved air vent 64e is schematically illustrated therein. Vent 64e comprises an outer rectangular box 86 having louvers, baffles, or windows 88 therein, within which box 86 is disposed a second box 89 with plastic sides enclosing a sandwich comprising a pair of plastic or metal screens 66e with a fibrous cellulosic or other type of filter 68e therebetween. Vent 64e with box 86 and screens 66e and filter 68e can be substituted for the vents, screens and filters previously described.

FIG. 15

Figure 15:
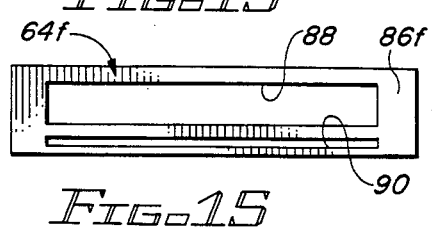
FIG. 15 is a schematic front elevation of a modified version of the array of FIG. 12.

A modified version of vent 64e is shown in FIG. 15. Thus, vent array 64f is shown which is identical to vent 64e except for having a bottom drain slit 90 in box 86f to allow liquid passing into box 86f to easily drain away. Vent array 64f is preferably used when large amounts of liquids are expected to be encountered in surgery. Thus, box 86f can be fitted into a suitable opening in the frame of the particular device 20a, 20b or 20d to be used in place of existing removable vents, screens and filters.

Various other modifications, changes, alterations and additions can be made in the improved device of the present invention, its components and parameters. All such changes, modifications, alterations and additions as are within the scope of the appended claims form part of the present invention.

What is claimed is:

1. An improved eye protection device to prevent eye contact with liquid and solid disease-bearing contaminants, said device comprising, in combination:

(a) a frame adapted to be seated over the eyes of a wearer and comprising a front support and a spaced pair of rearwardly extending side supports connected thereto;

(b) one or more transparent solid eye shields secured in said front support;

(c) means secured to said side supports for releasably sealing said frame and shield firmly in place on a wearer's head; and, (d) protective means connected to said frame to allow the transmission of air through said frame while blocking the passage of liquid and solid matter therethrough, (e) wherein said protective means comprises a pair of generally triangular sheets of flexible resilient material capable of transmitting air but blocking liquid or solid therethrough, said sheets being connected to said side supports and extending therebelow, and also connected to said front support to block passage of liquid and solid matter to the side of the wearer's eyes.

2. An improved eye protection device to prevent eye contact with liquid and solid disease-bearing contaminants, said device comprising, in combination:

(a) a frame adapted to be seated over the eyes of a wearer and comprising a front support and a spaced pair of rearwardly extending side supports connected thereto;

(b) one or more transparent solid eye shields secured in said front support;

(c) means secured to said side supports for releasably sealing said frame and shield firmly in place on a wearer's head; and, (d) protective means connected to said frame to allow the transmission of air through said frame while blocking the passage of liquid and solid matter therethrough, (e) wherein said protective means comprise a pair of generally triangular sheets of flexible resilient material capable of transmitting air but not liquid or solid therethrough said sheets being connected to said side supports and to said front support above said side supports to block passage of liquid and solid matter to the front and side of the wearer's eyes.

3. The improved device of claim 2 wherein said sheets are connected to slides releasably secured in channels in said side supports, whereby said sheets foldably slide along said channels to a stored position when said side supports are folded against said front support.

4. The improved device of claim 3 wherein said device is a pair of eyeglasses with hinged side supports and including a pair of triangular shaped flexible gas permeable side sheets connected to and depending from said side supports and side of said front support to block passage of liquid and solid contaminants to the eye.

5. The improved device of claim 4 wherein said side supports terminate in curved ear pieces, the front ends of which releasably slide in channels in said side supports to permit adjustment of said glasses for a snug sealing fit.

6. An improved eye protection device to prevent eye contact with liquid and solid disease-bearing contaminants, said device comprising, in combination:

(a) a frame adapted to be seated over the eyes of a wearer and comprising a front support and a spaced pair of rearwardly extending side supports connected thereto;

(b) one or more transparent solid eye shields secured in said front support;

(c) means secured to said side supports for releasably sealing said frame and shield firmly in place on a wearer's head; and, (d) protective means connected to said frame to allow the transmission of air through said frame while blocking the passage of liquids and solid matter therethrough, (e) wherein said device comprises prescription goggles, (f) wherein said frame is soft and flexible, (g) wherein said side supports are flexible adjustable straps, (h) wherein the lenses of said goggles are releasably secured in said frame, (i) wherein said frame includes air vents with filters therein to provide free passage of air while blocking liquid and solid transmission, (j) wherein said goggles bear means for shielding said vents against contact with liquid and solid contaminants, and (k) wherein said shielding means comprises a plate releasably attachable to said frame above said lenses and projecting forwardly thereof.

7. The improved device of claim 6 wherein said plate is attachable by screws holding said lenses in place in said goggles.

8. The improved device of claim 7 wherein said shielding means are hinged multi-position cover plates attached to said air vents.

9. An improved eye protection device to prevent eye contact with liquid and solid disease-bearing contaminants, said device comprising, in combination:

(a) a frame adapted to be seated over the eyes of a wearer and comprising a front support and a spaced pair of rearwardly extending side supports connected thereto;

(b) one or more transparent solid eye shields secured in said front support;

(c) means secured to said side supports for releasably sealing said frame and shield firmly in place on a wearer's head; and, (d) protective means connected to said frame to allow the transmission of air through said frame while blocking the passage of liquids and solid matter therethrough, (e) wherein said device is a mask adapted for wear directly over the eyes and over eyeglasses and comprising a single face plate set in said frame, with said side supports comprising adjustable straps, (f) wherein said face plate is removable, (g) wherein said frame bears padding on the inner surfaces thereof, (h) wherein a plurality of air vents bearing filters are disposed in said frame, said filters blocking passage of liquid and solids therethrough, (i) wherein each said air vent comprises a vented outer box and an inner box, the latter bearing a sandwich of a pair of screens with a flexible liquid and solid-blocking filter material therebetween.

10. The improved device of claim 9 wherein said outer box includes a bottom liquid-solid drain slit.

* * * * *